Figure 1:
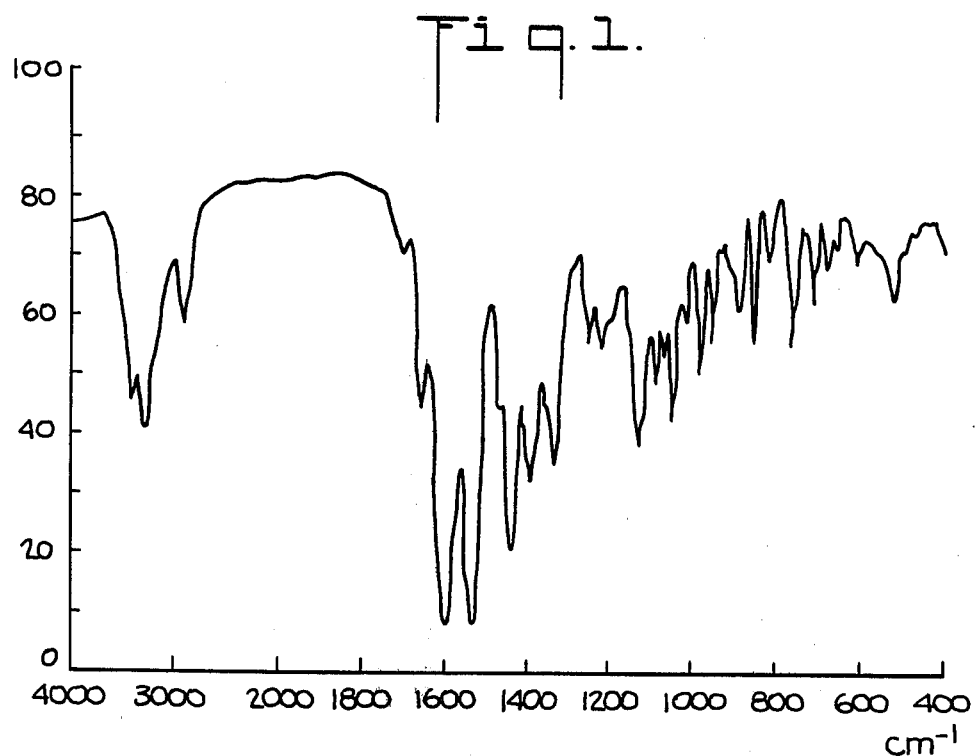

United States Patent [19]

Kasai et al.

[11] 4,374,774

[45] Feb. 22, 1983

[54] MITOMYCINS

[75] Inventors: Masaji Kasai, Fujisawa; Motomichi Kono; Kunikatsu Shirahata, both of Machida, all of Japan

[73] Assignee: Kyowa Hakko Kogyo Co., Ltd., Tokyo, Japan

[21] Appl. No.: 126,346

[22] Filed: Mar. 3, 1980

[30] Foreign Application Priority Data

Mar. 13, 1979 [JP] Japan .................................. 54/28250
Jun. 28, 1979 [JP] Japan .................................. 54/80809

[51] Int. Cl.³ .......................................... C07D 487/02
[52] U.S. Cl. .................................................. 548/422
[58] Field of Search ...................... 260/326.5 B, 326.24

[56]  References Cited

U.S. PATENT DOCUMENTS 3,641,053  2/1972  Uzu et al. ...................... 260/326.24
3,738,998  6/1973  Uzu et al. ...................... 260/326.24
4,159,266  6/1979  Kukelja ........................... 260/265.4

*Primary Examiner*—David B. Springer
*Attorney, Agent, or Firm*—Fitzpatrick, Cella, Harper & Scinto

[57]  ABSTRACT

New mitomycins are produced by synthetic processes. The compounds exhibit broad spectrum antibacterial activity and are useful as antibacterial agents.

5 Claims, 4 Drawing Figures

MITOMYCINS

BACKGROUND OF THE INVENTION

1. Field of the Invention

This invention relates to new mitomycins and processes for production thereof.

2. Description of Prior Art

Mitomycins are generally known as compounds having anti-tumor, antibacterial activity. Representative mitomycins include mitomycin A, mitomycin B, mitomycin C, and porfiromycin, which are described in the Merck Index (Ninth Edition). In addition, Japanese Published Unexamined Patent Application No. 122797/1979 describes other mitomycins viz. mitomycin D and mitomycin E. These known mitomycins may be obtained by culturing a strain of *Streptomyces caespitosus* and have the following chemical structures:

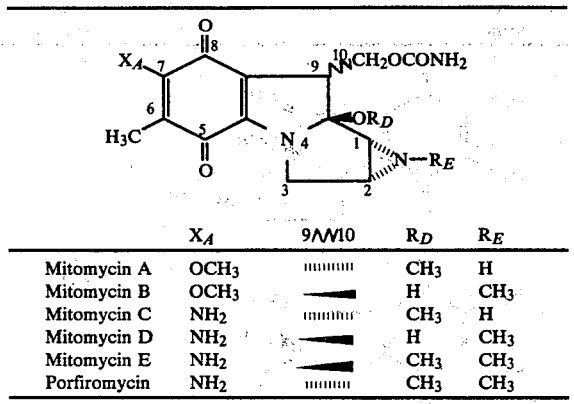

|              | $X_A$   | 9∧∧10    | $R_D$   | $R_E$   |
|--------------|---------|----------|---------|---------|
| Mitomycin A  | $OCH_3$ |          | $CH_3$  | H       |
| Mitomycin B  | $OCH_3$ |          | H       | $CH_3$  |
| Mitomycin C  | $NH_2$  |          | $CH_3$  | H       |
| Mitomycin D  | $NH_2$  |          | H       | $CH_3$  |
| Mitomycin E  | $NH_2$  |          | $CH_3$  | $CH_3$  |
| Porfiromycin | $NH_2$  |          | $CH_3$  | $CH_3$  |

Various derivatives of these compounds are also known. For example, 1a-N-acetyl-mitomycin C (U.S. Pat. No. 3,514,452), 1a-N-butyryl-mitomycin C (U.S. Pat. No. 3,514,452), 7-ethylamino-7-demethoxy-mitomycin A (U.S. Pat. No. 3,514,452), 10-decarbamoyl-mitomycins A, B and C (U.S. Pat. No. 3,738,998) 1a-N-acetyl-10-decarbamoyl-mitomycin C (Japanese Published Examined Patent Application No. 17,279/1974), 1a-N-acetyl-10-decarbamoyl-10-p-toluene-sulfonyl-mitomycin C (Japanese Published Examined Patent Application No. 37,639/1972), 10-decarbamoyl-10-p-toluene-sulfonyl-porfiromycin (Japanese Published Examined Patent Application No. 37,639/1972), etc. are known. In addition, mitomycins having a double bond between 9- and 10-positions, other than those described in the present specification, are disclosed in commonly owned U.S. Patent Application Ser. No. 58,670 filed on July 18, 1979.

While the known mitomycins exhibit good activity, new antibacterial compounds are always in demand. To this end, the present inventors have found new mitomycins which exhibit good antibacterial activity.

SUMMARY OF THE INVENTION

In accordance with the present invention, new mitomycins are produced having the general formula [I] (hereinafter sometimes referred to as Compound [I]. Compounds of other formulae are similarly identified.)

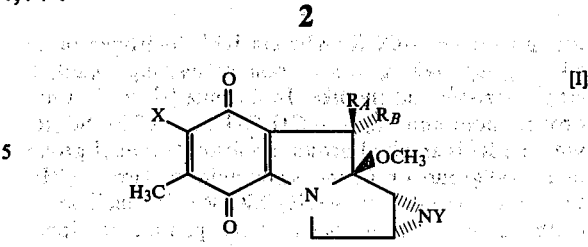

wherein X is an amino group, a substituted amino group, a hydroxy group or an alkoxy group; Y is a hydrogen atom, a methyl group, —$COR^1$ wherein $R^1$ is a hydrogen atom, an alkyl group, a substituted alkyl group, an aryl group or a substituted aryl group, or —$CH_2CH_2Z$ wherein Z is an alkoxycarbonyl group, an acyl group or a cyano group; and $R_A$ is a hydrogen atom and $R_B$ is —$CH_2OH$ or —$CH_2OSO_2R^2$ wherein $R^2$ is an alkyl group, a substituted alkyl group or an aryl group, or $R_A$ and $R_B$ combine to form =$CH_2$. Notwithstanding the above definition, when $R_A$ is a hydrogen atom and $R_B$ is —$CH_2OH$, Y is —$CH_2CH_2Z$, when $R_A$ is a hydrogen atom and $R_B$ is —$CH_2OSO_2R^2$, Y is a hydrogen atom or —$CH_2CH_2Z$ and when Y is a methyl group, X is a hydroxy group and $R_A$ and $R_B$ combine to form =$CH_2$.

The invention also pertains to various synthetic processes for producing Compound [I].

The compounds of the present invention (Compound [I]) have broad antibacterial activity and are, therefore, useful to clean and sterilize laboratory glassware and surgical instruments. The compounds may also be used in combination with soaps, detergents and wash solutions for sanitary purposes. Compound [I] may also be useful as medicaments or intermediates in the preparation of other mitomycin derivatives having similar activity.

DESCRIPTION OF THE INVENTION

Compounds of the present invention are represented by the general formula [I]:

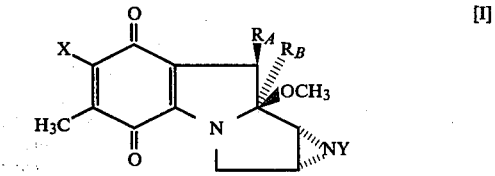

In formula [I], X is an amino group, a substituted amino group, a hydroxy group or an alkoxy group. The term "alkoxy" group includes an alkoxy group having 1–4 carbon atoms, e.g., methoxy, ethoxy, i-propoxy, n-butoxy, t-butoxy and the like. Y is a hydrogen atom, a methyl group, —$COR^1$ or —$CH_2CH_2Z$. In the representation —$COR^1$, $R^1$ is a hydrogen atom, an alkyl group, a substituted alkyl group, an aryl group or a substituted aryl group. The term "alkyl" group includes an alkyl group having 1–3 carbon atoms, e.g., methyl, ethyl, i-propyl and the like; the term "substituted alkyl" group includes chloromethyl and the like; the term "aryl" group includes phenyl and the like; and the term "substituted aryl" group includes p-methoxyphenyl and the like. In the representation —$CH_2CH_2Z$, Z is an alkoxycarbonyl group, an acyl group or a cyano group. The alkyl group of the term "alkoxycarbonyl" group includes an alkyl group having 1–4 carbon atoms, e.g., methyl, ethyl, t-butyl and the like; and the term "acyl"

group includes —COR⁴ wherein R⁴ is hydrogen or an alkyl group having 1-3 carbon atoms, e.g., methyl, ethyl, i-propyl and the like. In formula [I], $R_A$ is a hydrogen atom and $R_B$ is —CH₂OH or —CH₂OSO₂R² wherein R² is an alkyl group, a substituted alkyl group or an aryl group, or $R_A$ and $R_B$ combine to form =CH₂. In the representation —CH₂OSO₂R², R² includes a methyl group, a trifluoromethyl group, a p-methylphenyl group and the like. Notwithstanding the above definition, when $R_A$ is a hydrogen atom and $R_B$ is —CH₂OH, Y is —CH₂CH₂Z; when $R_A$ is hydrogen and $R_B$ is —CH₂OSO₂R², Y is a hydrogen atom or —CH₂CH₂Z; and when Y is a methyl group, X is a hydroxy group and $R_A$ and $R_B$ combine to form =CH₂.

The most preferred compounds of the present invention (Compound [I]) have a double bond between the 9- and 10-positions and are represented by the general formula [I']

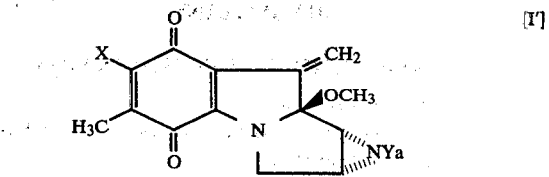

wherein when Ya is a hydrogen atom, X has the same meaning as defined before and when Ya is a methyl group, X is a hydroxy group.

Specific examples of Compound [I] are set forth in the following Table. The physical properties of the compounds as well as processes for synthesis thereof are set forth in the examples identified. The compound numbers are also sometimes used in the description which follows to identify that particular compound.

| No. of compound | Name of compound | Structural formula | No. of example |
|---|---|---|---|
| 1 | 1a-N—acetyl-10-decarbamoyloxy-9-dehydro-mitomycin C | | 1 |
| 2 | 10-decarbamoyloxy-9-dehydro-mitomycin C | | 2,6, 8,11 |
| 3 | 7-deamino-10-decarbamoyloxy-9-dehydro-7-hydroxy-mitomycin C | | 9 |
| 4 | 10-decarbamoyloxy-9-dehydro-mitomycin A | | 10 |
| 5 | 10-decarbamoyl-10-methanesulfonyl-mitomycin C | | 7 |
| 6 | 10-decarbamoyl-1a-N—(2-formyl-ethyl)-10-methanesulfonyl-mitomycin C | | 4 |

-continued

| No. of compound | Name of compound | Structural formula | No. of example |
|---|---|---|---|
| 7 | 10-decarbamoyl-1a-N—(2-formyl-ethyl)-mitomycin C | | 3 |
| 8 | 10-decarba-moyloxy-9-dehydro-1a-N—(2-formyl-ethyl)-mitomycin C | | 5 |
| 9 | 10-decarba-moyloxy-9-dehydro-7-deamino-7-hydroxy-porfiromycin | | 12 |

The minimum inhibitory concentration (μg/ml) (agar dilution method, pH 7.0) of the foregoing compounds against various bacteria identified below is illustrated in the following Tables.

A: *Serratia marcescens* ATCC 4003
B: *Pseudomonas cepacia* ATCC 25608
C: *Staphylococcus aureus* ATCC 6538P
D: *Escherichia coli* ATCC 26
E: *Bacillus subtilis* No. 10707
F: *Proteus vulgalis* ATCC 6897
G: *Shigella sonnei* ATCC 9290
H: *Salmonella typhosa* ATCC 9992
I: *Klebsiella pneumoniae* ATCC 10031

TABLE 1

| Test compound | Bacteria | | | | | | | | |
|---|---|---|---|---|---|---|---|---|---|
| | A | B | C | D | E | F | G | H | I |
| Compound 1 | >200 | >200 | 200 | — | 6.3 | 200 | — | >200 | 50 |
| Mitomycin C | 2.5 | >10 | 0.16 | 5.0 | 0.039 | 0.078 | 1.3 | 5.0 | 0.020 |

TABLE 2

| Test compound | Bacteria | | | | | | | | |
|---|---|---|---|---|---|---|---|---|---|
| | A | B | C | D | E | F | G | H | I |
| Compound 2 | >11 | >11 | 2.6 | — | 0.041 | 1.3 | — | >11 | 0.66 |
| Compound 3 | >8.6 | >8.6 | 4.3 | — | 0.54 | 4.3 | — | >8.6 | 4.3 |
| Compound 4 | >150 | >150 | 9.4 | >150 | 0.59 | 9.4 | — | >150 | 4.7 |
| Compound 5 | >170 | 83 | 42 | — | 42 | 170 | — | >170 | 42 |
| Compound 6 | >200 | 50 | 50 | — | 50 | 100 | >200 | >200 | >200 |
| Compound 7 | 220 | 54 | 3.4 | 220 | 6.8 | 6.8 | 110 | 54 | 6.8 |
| Mitomycin C | 5.6 | 5.6 | 0.087 | >11 | 0.044 | 0.087 | 5.6 | 5.6 | 0.011 |

TABLE 3

| Test compound | Bacteria | | | | | | | | |
|---|---|---|---|---|---|---|---|---|---|
| | A | B | C | D | E | F | G | H | I |
| Compound 8 | >50 | 50 | 13 | — | 0.39 | 25 | — | >50 | 13 |
| Mitomycin C | 2.5 | 10 | 0.039 | >10 | 0.020 | 0.039 | 5 | 2.5 | 0.0098 |

TABLE 4
| Test compound | Bacteria | | | | | | | | |
|---|---|---|---|---|---|---|---|---|---|
| | A | B | C | D | E | F | G | H | I |
| Compound 9 | >200 | — | 100 | 200 | >0.098 | 25 | 200 | 50 | 6.3 |
| Compound | >200 | — | 100 | — | 0.195 | 100 | >200 | — | 3.1 |
TABLE 4-continued
| Test compound | Bacteria | | | | | | | | |
|---|---|---|---|---|---|---|---|---|---|
| | A | B | C | D | E | F | G | H | I |
| A* | | | | | | | | | |
Processes for the production of Compounds [I] are exemplified by the following flow diagram.
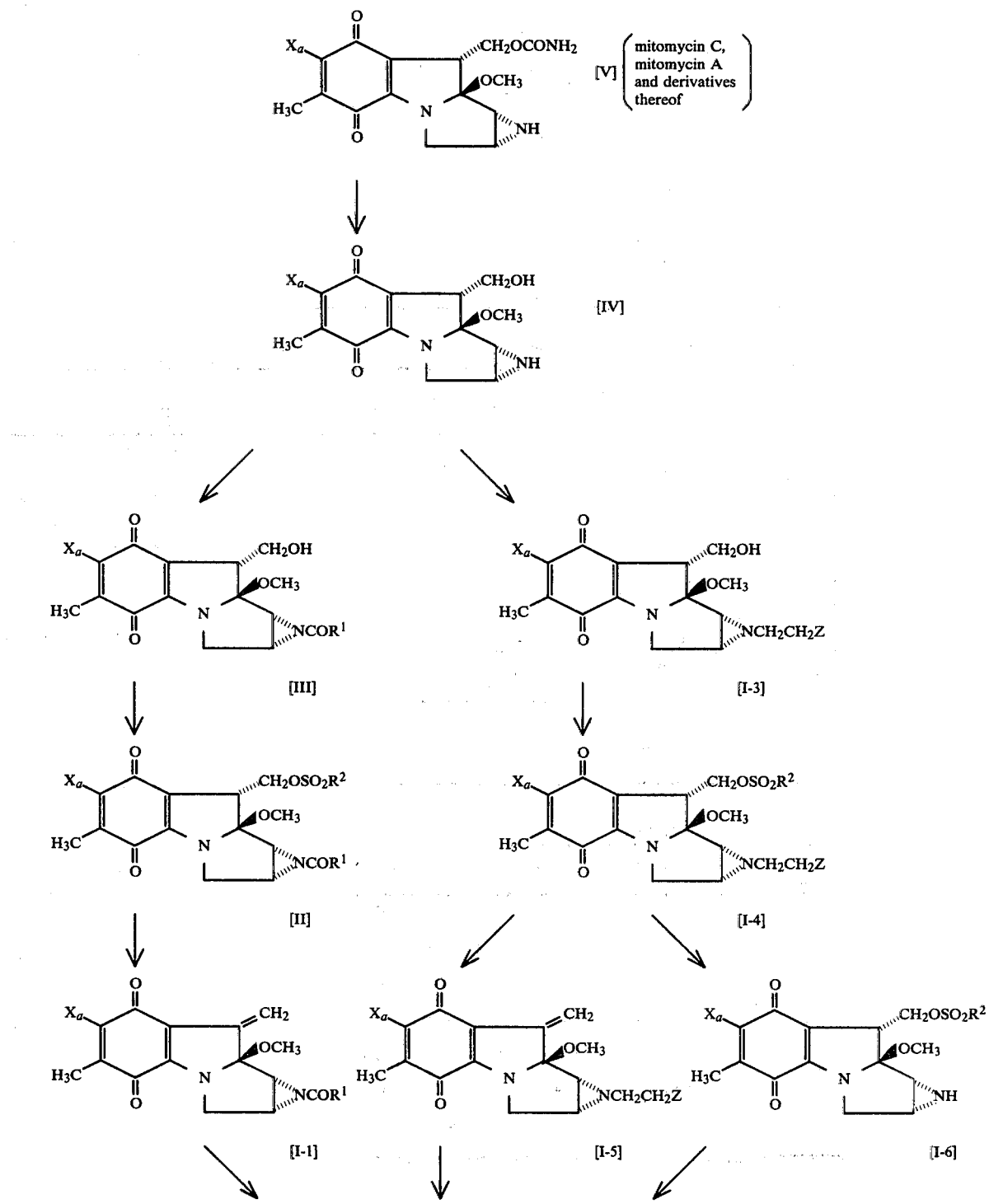

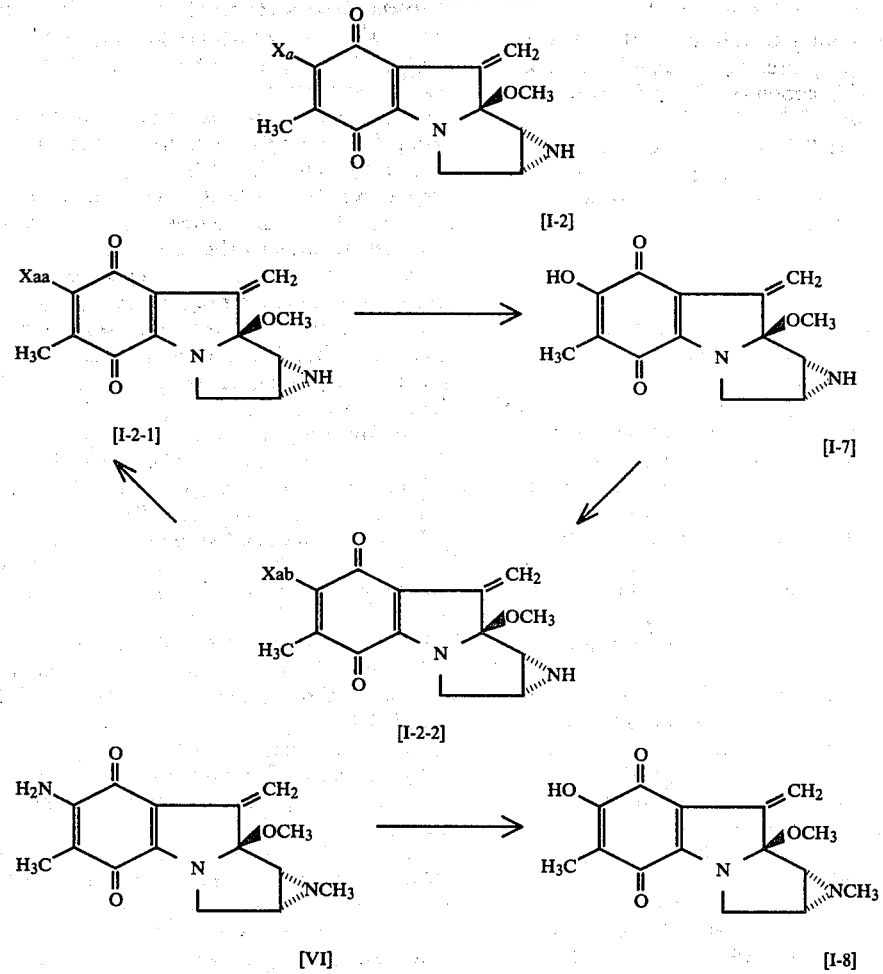

In the above processes, Xa is an amino group, a substituted amino group or an alkoxy group (Xa=X where X≠hydroxy). Xaa is amino or substituted amino (Xaa=Xa where Xa≠alkoxy). Xab is alkoxy (Xab=Xa where Xa≠amino or substituted amino). $R^1$, $R^2$ and Z have the same meaning as defined before.

Compounds [I-1]-[I-8] are included in Compound [I]. Compounds [I-2-1] and [I-2-2] are included in Compound [I-2]. Compounds [II]-[V] are known compounds. Compound [VI] is disclosed in U.S. Patent Application Ser. No. 58,670, filed July 18, 1979.

Each of the above processes is described below.

Process of Compound [V]→Compound [IV]

Included in Compound [V] are Mitomycin C wherein Xa is an amino group and Mitomycin A wherein Xa is a methoxy group. A compound included in Compound [V] wherein Xa is an alkoxy group and a process for production thereof are disclosed in U.S. Pat. No. 3,558,651. A compound included in Compound [V] wherein Xa is a substituted amino group and a process for production thereof are disclosed in J. Med. Chem., 14, 103 (1971).

Compound [IV] is also known and may be obtained by a lithium aluminum hydride method (U.S. Pat. No. 3,738,998); hydrolysis by alklai (U.K. Pat. No. 1,250,063; a sodium alcoholate method [U.K. Pat. No. 1,250,063; J. Med. Chem., 14, 109 (1971)]; and by other like methods.

A sodium alcoholate method which is illustrated in Reference Example 1 is briefly described below.

Compound [IV] is obtained by eliminating carbamoyl from Compound [V] in the presence of an alcoholate in a solvent inert to the reaction. Suitable alcoholates for the reaction include alcoholates of methanol, ethanol, t-butanol and the like with sodium, potassium, and the like. Suitable solvents include methanol, ethanol, i-propanol, tetrahydrofuran, dioxane, dimethylformamide, benzene and the like. Preferably 5 to 7 times alcoholate is used per mole of Compound [V]. The reaction is usually carried out at room temperature and completed in several hours to several days.

Process of Compound [IV]→Compound [III]

Compound [III] is obtained by reacting Compound [IV] with a reactive derivative of a carboxylic acid represented by the general formula $R^1COOH$ wherein $R^1$ has the same meaning as defined before, such as an acid halide, an acid anhydride and the like (hereinafter referred to as an acylating agent), in the presence of a base in an inert solvent.

Suitable acylating agents for the reaction include acetyl chloride, propionyl chloride, acetic anhydride and the like. Suitable bases include sodium carbonate, sodium hydride, triethylamine, pyridine and the like. Suitable solvents include tetrahydrofuran, dioxane, chloroform and the like. Certain bases, such as pyridine, may also function as the solvent.

Preferably 1 to 2 times acylating agent is used per mole of Compound [IV]. Preferably 1 to 100 times base is used per mole of Compound [IV]. The reaction is usually carried out at −78° to 30° C.

Process of Compound [III]→Compound [II]

Compound [II] is obtained by reacting Compound [III] with a reactive derivative of a compound represented by the general formula $$R^2SO_2OH$$

wherein $R^2$ has the same meaning as defined before (hereinafter referred to as a sulfonylating agent), in the presence of a base in an inert solvent.

Suitable sulfonylating agents for the reaction include halides, acid anhydrides and the like of the compound represented by the above general formula, such as methanesulfonyl chloride, trifluoromethanesulfonyl chloride, p-toluenesulfonyl chloride and the like. Suitable bases include inorganic bases such as sodium carbonate, sodium hydride and the like and organic bases such as triethylamine, pyridine and the like. These organic bases also function as the solvent. Suitable solvents include tetrahydrofuran, dioxane, chloroform and the like.

Typically, 1 to 2 times sulfonylating agent is used per mole of Compound [III]. The base is typically used in an amount of 1 to 100 times per mole of Compound [III]. The reaction is usually carried out at −78° to 30° C.

Process of Compound [II]→Compound [I-1]

Compound [I-1] is obtained by eliminating alkyl (or aryl)-sulfonic acid from Compound [II] in the presence of a base in an inert solvent.

Suitable bases for the reaction include inorganic bases such as sodium hydroxide, sodium hydride and the like and organic bases such as potassium-t-butoxide, 1,5-diazabicyclo[5.4.0]undecene-5, triethylamine, sodium methoxide, preferably potassium t-butoxide, 1,5-diazabicyclo[5.4.0]-undecene-5 and the like. Suitable solvents include ethyl ether, tetrahydrofuran, dioxane, ethylene glycol dimethyl ether, n-hexane, petroleum ether, benzene, N,N-dimethylformamide, ethyl acetate, acetone, methylene chloride, dimethylsulfoxide and the like.

The base is typically used in an amount of 1 to 20 times per mole of Compound [II]. The reaction is generally carried out at 0° to 80° C. and is usually completed in one hour to one week.

Process of Compound [I-1]→Compound [I-2]

Compound [I-2] is obtained by hydrolyzing Compound [I-1] in the presence of a base in water and an inert solvent.

Suitable bases for the reaction include sodium hydrogen carbonate, ammonia, diethylamine, hydrazine and the like. Suitable inert solvents include methanol, ethanol, tetrahydrofuran, dimethylformamide, ethyl acetate, acetone, chloroform and the like.

The base is typically used in an amount of 1 to 20 times per mole of Compound [I-1]. The reaction is generally carried out at 0° to 60° C. and usually completed in 1 to 10 hours.

Process of Compound [IV]→Compound [I-3]

Compound [I-3] is obtained by reacting Compound [IV] with a compound represented by the general formula $$CH_2=CHZ$$

wherein Z has the same meaning as defined before (hereinafter referred to as an alkylating agent) in an inert solvent to alkylate the 1a-N-position of Compound [IV].

When an alkylating agent active to the reaction (for example, acrolein) is used, the reaction proceeds simply by mixing the agent with Compound [IV]. Nevertheless, the reaction is usually carried out in the presence of a base such as triethylamine, sodium methoxide, potassium t-butoxide, and the like so that the reaction proceeds smoothly. Suitable solvents for the reaction include ethyl ether, tetrahydrofuran, dioxane, ethylene glycol dimethyl ether, n-hexane, petroleum ether, benzene, N,N-dimethylformamide, ethyl acetate, acetone, methylene chloride, chloroform, dimethylsulfoxide and the like.

The alkylating agent is typically used in an amount of 1 to 30 times per mole of Compound [IV].

The reaction is carried out preferably at 20° to 80° C. and usually completed in one hour to one week.

The alkylating method used in this process is known as a Michael addition and is disclosed in "Ethylenimine and Other Aziridines" 136, 1969 (Academic Press, U.S.A.).

Process of Compound [I-3]→Compound [I-4]

Compound [I-4] is obtained in the same manner as described in the process of Compound [III]→Compound [II].

Process of Compound [I-4]→Compound [I-5]

Compound [I-5] is obtained in the same manner as described in the process of Compound [II]→Compound [I-1].

Process of Compound [I-5]→Compound [I-2]

Compound [I-2] is obtained by subjecting Compound [I-5] to retro Michael reaction in the presence of an acid or a base in an inert solvent.

Suitable acids for the reaction include inorganic acids such as perchloric acid, and the like. Suitable bases include tertiary amines such as N,N-dimethylaniline, and the like. Suitable solvents include ethyl ether, tetrahydrofuran, ethylene glycol dimethyl ether, n-hexane, pertroleum ether, benzene, N,N-dimethylformamide, ethyl acetate, acetone, methylene chloride, chloroform, dimethylsulfoxide and the like.

The acid or base is typically used in an amount of 1 to 100 times per mole of Compound [I-5].

The reaction is preferably carried out at 0° to 80° C. and usually completed in 10 minutes to several hours.

Retro Michael reaction is disclosed in Tetrahedron Letters, No. 49, 4295 (1977), Synthesis, No. 12, 745 (1973).

Process of Compound [I-4]→Compound [I-6]

Compound [I-6] is obtained in the same manner as described in the process of Compound [I-5]→Compound [I-2].

Process of Compound [I-6]→Compound [I-2]

Compound [I-2] is obtained in the same manner as described in the process of Compound [II]→Compound [I-1].

Process of Compound [I-2-1]→Compound [I-7]

Compound [I-7] is obtained by hydrolizing Compound [I-2-1] in an aqueous solution of a base.

Suitable bases include inorganic bases such as sodium hydroxide, sodium carbonate and the like and organic bases such as triethylamine and the like.

The base is usually used in a concentration of 0.01 to 1 normality. The reaction is usually carried out at room temperature and completed in 30 minutes to several hours.

Process of Compound [I-7]→Compound [I-2-2]

Compound [I-2-2] is obtained by reacting Compound [I-7] with an alkylating agent in an inert solvent.

Suitable alkylating agents for the reaction include diazoalkanes such as diazomethane and the like, alkyl halides such as methyl iodide and the like, dialkyl sulfates such as dimethyl sulfate and the like. Suitable solvents include ethyl acetate, ethyl ether and the like. When an acid is produced by the reaction, the reaction is carried out in the presence of an acid acceptor such as potassium carbonate, triethylamine and the like.

Process of Compound [I-2-2]→Compound [I-2-1]

Compound [I-2-1] is obtained by reacting Compound [I-2-2] with ammonia or an amine in an inert solvent such as methanol and the like.

The ammonia or amine is typically used in an amount of 1 to 100 times per mole of Compound [I-2-2]. The reaction is usually carried out at 20° to 80° C. and completed in 1 to several hours.

Process of Compound [VI]→Compound [I-8]

Compound [I-8] is obtained in the same manner as described in the process of Compound [I-2-1]→Compound [I-7].

Although Compound [VI] and preparation thereof are disclosed in U.S. Patent Application Ser. No. 58,670 filed July 18, 1979, the preparation is illustrated in Reference Example 4.

In each of the above processes, recovery of the desired compound from the reaction mixture is carried out by conventional methods such as those described in the following Examples and Reference Examples.

Certain specific embodiments of the invention are illustrated by the following representative examples.

EXAMPLE 1

Preparation of Compound [I-1] from Compound [II]

In this example, 38 mg of 1a-N-acetyl-10-decarbamoyl-10-methanesulfonyl-mitomycin C obtained in Reference Example 3 is dissolved in 8 ml of ethylene glycol dimethyl ether. Then, 150 mg of 1,5-diazabicyclo[5.4.0]undecene-5 is added to the solution and the mixture is refluxed with heating for 2 hours in an atmosphere of nitrogen. The reaction mixture is then poured in saturated aqueous solution of sodium hydrogen carbonate and the mixture is extracted with ethyl acetate. The extract is washed with water, dried with anhydrous sodium sulfate and concentrated under reduced pressure to remove the solvent. The residue is then purified by silica gel column chromatography using a mixed solvent of chloroform and acetone (6:4) (volume ratio, as is the same hereinafter) as a developer to obtain 24 mg of deep green crystals having the following physical properties:

Mass spectrum:

The substance exhibits molecular ion peak at m/e 315

$^1$HNMR spectrum (in pyridine-d$_5$, δ (ppm)):
2.03(s,3H), 2.05(s,3H), 3.17(s,3H), 3.57(dd,1H), 3.64(dd,1H), 3.78(d,1H), 4.84(d,1H), 5.61(d,1H), 6.55(d,1H), 7.76(bs,2H)

IR spectrum (KBr tablet, cm$^{-1}$):
3435(w), 3330(m) (N-H stretch), 1695(s), 1594(vs), 1537(vs) (C=O stretch), 1656(m) (C=C stretch)

From the above properties, the substance is identified as 1a-N-acetyl-10-decarbamoyloxy-9-dehydro-mitomycin C. Yield 82%.

EXAMPLE 2

Preparation of Compound [I-2] from Compound [I-1]

In this example, 57 mg of 1a-N-acetyl-10-decarbamoyloxy-9-dehydro-mitomycin C is dissolved in 1 ml of methanol. Then, 1 ml of 10% aqueous solution of sodium hydrogen carbonate is added to the solution and the mixture is stirred at room temperature for 6 hours. After the completion of the reaction, the reaction mixture is extracted with ethyl acetate. The extract is then dried with anhydrous sodium sulfate and concentrated under reduced pressure.

The residue is purified by silica gel column chromatography using a mixed solvent of chloroform and acetone (1:1) to obtain 36 mg of deep green crystals having the following physical properties: Mass spectrum:

The substance exhibits molecular ion peak at m/e 273. Molecular weight obtained by high resolution mass spectrometry is 273.1130 (273.1113 as calculated).

$^1$HNMR spectrum (in pyridine-d$_5$, δ (ppm)):
2.00(s,3H), 2.77(dd,1H), 3.04(d,1H), 3.17(s,3H), 3.59(dd,1H), 4.67(d,1H), 5.50(d,1H), 6.50(d,1H), 7.57(bs,2H)

IR spectrum (KBr tablet, cm$^{-1}$) (FIG. 1): 3420(m) (N-H stretch), 3320(m) (N-H stretch), 3285(m) (N-H stretch), 1651(m) (C=C stretch), 1592(vs) (C=O stretch), 1532(vs) (C=O stretch)

From the foregoing properties, the substance is identified as 10-decarbamoyloxy-9-dehydro-mitomycin C. Yield 73%.

EXAMPLE 3

Preparation of Compound [I-3] from Compound [IV]

In this example, 66 mg of 10-decarbamoyl-mitomycin C obtained in Reference Example 1 is dissolved in 5 ml of methylene chloride. Then, 0.3 ml of acrolein (purity 90%) is added to the solution. The mixture is then stirred at room temperature for 4 days and concentrated under reduced pressure. The residue is purified by silica gel column chromatography using a mixed solvent of chloroform and methanol (93:7) to obtain 76 mg of purplish black crystals having the following physical properties:

$^1$HNMR spectrum (in pyridine-d$_5$, δ (ppm)):
2.00(s,3H), 2.39–2.96(m,4H), 2.40(dd,1H), 2.91(d,1H) 3.22(s,3H), 3.61(dd,1H), 3.83(dd,1H), 4.34(dd,1H), 4.49(d,1H), 4.75(dd,1H), 6.18(bs,1H), 7.58(bs,2H), 9.76(t,1H)

IR spectrum (KBr tablet, cm$^{-1}$): 3430(m) (N-H stretch), 3335(m) (N-H stretch), 1722(m) (C=O stretch), 1604(s) (C=O stretch), 1554(vs) (C=O stretch)

From the foregoing properties, the substance is identified as 10-decarbamoyl-1a-N-(2-formylethyl)-mitomycin C. Yield 97%.

EXAMPLE 4

Preparation of Compound [I-4] from Compound [I-3]

In this example, 62 mg of 10-decarbamoyl-1a-N-(2-formylethyl)-mitomycin C obtained in Example 3 is dissolved in 0.33 ml of anhydrous pyridine. Then, 15 μl of methanesulfonyl chloride is added to the solution in an atmosphere of nitrogen and the mixture is stirred under ice cooling and sodium chloride for 2 hours. The reaction mixture is then poured into a saturated aqueous solution of sodium hydrogen carbonate and the mixture is extracted with chloroform. The extract is then washed with water, dried with anhydrous sodium sulfate and concentrated under reduced pressure. The residue is purified by silica gel column chromatography using a mixed solvent of chloroform and acetone (6:4) to obtain 44 mg of brownish black crystals having the following physical properties:

$^1$HNMR spectrum (in pyridine-d$_5$, δ ppm): 1.99(s,3H), 2.17–2.35(m,2H), 2.46(dd,1H), 2.64(dt,2H), 2.84(d,1H), 3.20(s,3H), 3.35(s,3H), 3.59(dd,1H), 4.01(dd,1H), 4.47(d,1H), 4.88(dd,1H), 5.37(dd,1H), 7.66(bs,2H), 9.75(t.1H)

IR spectrum (KBr tablet, cm$^{-1}$): 3440(m) (N-H stretch), 3340(m) (N-H stretch), 1720(m) (C=O stretch), 1604(vs) (C=O stretch), 1555(vs) (C=O stretch), 1351(vs) (antisym. SO$_2$, stretch), 1174(vs) (sym. SO$_2$, stretch)

From the foregoing properties, the substance is identified as 10-decarbamoyl-1a-N-(2-formylethyl)-10-methansulfonyl-mitomycin C. Yield 58%.

EXAMPLE 5

Preparation of Compound [I-5] from Compound [I-4]

In this example, 52 mg of 10-decarbamoyl-1a-N-(2-formylethyl)-10-methanesulfonyl-mitomycin C obtained in Example 4 is dissolved in 10 ml of anhydrous ethylene glycol dimethyl ether. Then, 210 mg of 1,5-diazabicylo [5.4.0] undecene-5 is added to the solution and the mixture is refluxed in an atmosphere of nitrogen for 2 hours. The reaction mixture is then poured into a saturated aqueous solution of sodium hydrogen carbonate and the mixture is extracted with ethyl acetate. The extract is washed with water, dried with anhydrous sodium sulfate and concentrated under reduced pressure. The residue is purified by silica gel column chromatography using a mixed solvent of chloroform and acetone (6:4) to obtain 16 mg of deep green crystals having the following physical properties:

$^1$HNMR spectrum (in pyridine-d$_5$, δ (ppm)): 2.00(s,3H), 2.29–2.78(m,4H), 2.40(dd,1H), 2.66(d,1H), 3.14(s,3H), 3.53(dd,1H), 4.64(d,1H), 5.51(d,1H), 6.51(d,1H), 7.68(bs,2H), 9.71(t,1H)

IR spectrum (KBr tablet, cm$^{-1}$): 3420(m) (N-H stretch), 3225(m) (N-H stretch), 1718(m) (C=O stretch), 1649(m) (C=C stretch), 1592(vs) (C=O stretch), 1535(vs) (C=O stretch)

From the foregoing properties, the substance is identified as 10-decarbamoyloxy-9-dehydro-1a-N-(2-formylethyl)mitomycin C. Yield 40%.

EXAMPLE 6

Preparation of Compound [I-2] from Compound [I-5]

In this example, 26 mg of 10-decarbamoyloxy-9-dehydro-1a-N-(2-formylethyl)-mitomycin C obtained in Example 5 is dissolved in 4 ml of anhydrous methylene chloride. Thereupon, first 100 mg of a salt of N,N-dimethylaniline with perchloric acid and subsequently 0.4 ml of N,N-dimethylaniline are added to the solution. The mixture is stirred at room temperature for 15 minutes and poured into a saturated aqueous solution of sodium hydrogen carbonate. The mixture is then extracted with chloroform. The extract is washed with water, dried with anhydrous sodium sulfate and concentrated under reduced pressure. The residue is purified by silica gel column chromatography using a mixed solvent of chloroform and acetone (1:1) to obtain 15 mg of deep green crystals.

Mass spectrum, $^1$HNMR spectrum and IR spectrum of the substance are in accord with those of the compound obtained in Example 2. Therefore, the substance is identified as 10-decarbamoyloxy-9-dehydro-mitomycin C. Yield 70%.

EXAMPLE 7

Preparation of Compound [I-6] from Compound [I-4]

In this example, 33 mg of 10-decarbamoyl-1a-N-(2-formylethyl)-10-methanesulfonyl-mitomycin C obtained in Example 4 is dissolved in 5 ml of anhydrous methylene chloride. Thereupon, first 120 mg of a salt of N,N-dimethylaniline with perchloric acid and subsequently 0.5 ml of N,N-dimethylaniline are added to the solution. The mixture is stirred at room temperature for 30 minutes. The reaction mixture is poured into a saturated aqueous solution of sodium hydrogen carbonate and the mixture is extracted with chloroform. The extract is then washed with water, dried with anhydrous sodium sulfate and concentrated under reduced pressure. The residue is purified by silica gel column chromatography using a mixed solvent of chloroform and methanol (97:3) to obtain 21 mg of purplish red crystals having the following physical properties:

$^1$HNMR spectrum (in pyridine-d$_5$, δ(ppm)): 2.04(s,3H), 2.82(dd,1H), 3.22(s,3H), 3.23(d,1H), 3.63 (dd,1H), 4.02(dd,1H), 4.52(d,1H), 5.18(dd,1H), 5.32(dd,1H), 7.66(bs,2H)

IR spectrum (KBr tablet, cm$^{-1}$): 3440(w) (N-H stretch), 3315(m)(N-H stretch), 1604(vs) (C=O stretch), 1555(vs)(C=O stretch), 1352(vs) (antisym. SO$_2$, stretch), 1174(vs) (sym. SO$_2$, stretch)

From the foregoing properties, the substance is identified as 10-decarbamoyl-10-methanesulfonyl-mitomycin C. Yield 72%.

EXAMPLE 8

Preparation of Compound [I-2] from Compound [I-6]

In this example, 20.5 mg of 10-decarbamoyl-10-methanesulfonyl-mitomycin C obtained in Example 7 is dissolved in 0.3 ml of anhydrous tetrahydrofuran. Then, 30 mg of 1,5-diazabicyclo[5.4.0] undecene-5 is added to the solution and the mixture is stirred at room temperature for 40 hours. The reaction mixture is then poured into a saturated aqueous solution of sodium hydrogen carbonate and the mixture is extracted with ethyl acetate. The extract is washed with water, dried with anhydrous sodium sulfate and concentrated under reduced pressure. The residue is then purified by silica gel column chromatography using a mixed solvent of chloroform and acetone (1:1) to obtain 1.2 mg of deep green crystals.

Mass spectrum, $^1$HNMR spectrum and IR spectrum of the substance are in accord with those of the compound obtained in Example 2. Therefore, the substance is identified as 10-decarbamoyloxy-9-dehydro-mitomycin C. Yield 7.9%.

EXAMPLE 9

Preparation of Compound [I-7] from Compound [I-2-1]

In this example, 18 mg of 10-carbamoyloxy-9-dehydro-mitomycin C obtained in Example 2 is dissolved in 3.75 ml of 0.1N sodium hydroxide. The solution is stirred at room temperature for 45 minutes. The reaction solution is then adjusted to pH 4 with diluted hydrochloric acid and extracted with ethyl acetate. The extract is washed with water, dried with anhydrous sodium sulfate and concentrated under reduced pressure. The residue is then purified by silica gel column chromatography using a mixed solvent of chloroform and methanol (9:1) to obtain 12 mg of purplish black crystals having the following physical properties:

Mass spectrum:

The substance exhibits molecular ion peak at m/e 274.

$^1$HNMR spectrum (in pyridine-d$_5$, δ(ppm)): 2.05(s,3H), 2.80(dd,1H), 3.08(d,1H), 3.19(s,3H), 3.58(dd,1H), 4.50(d,1H), 5.55(d,1H), 6.52(d,1H)

Figure 2:
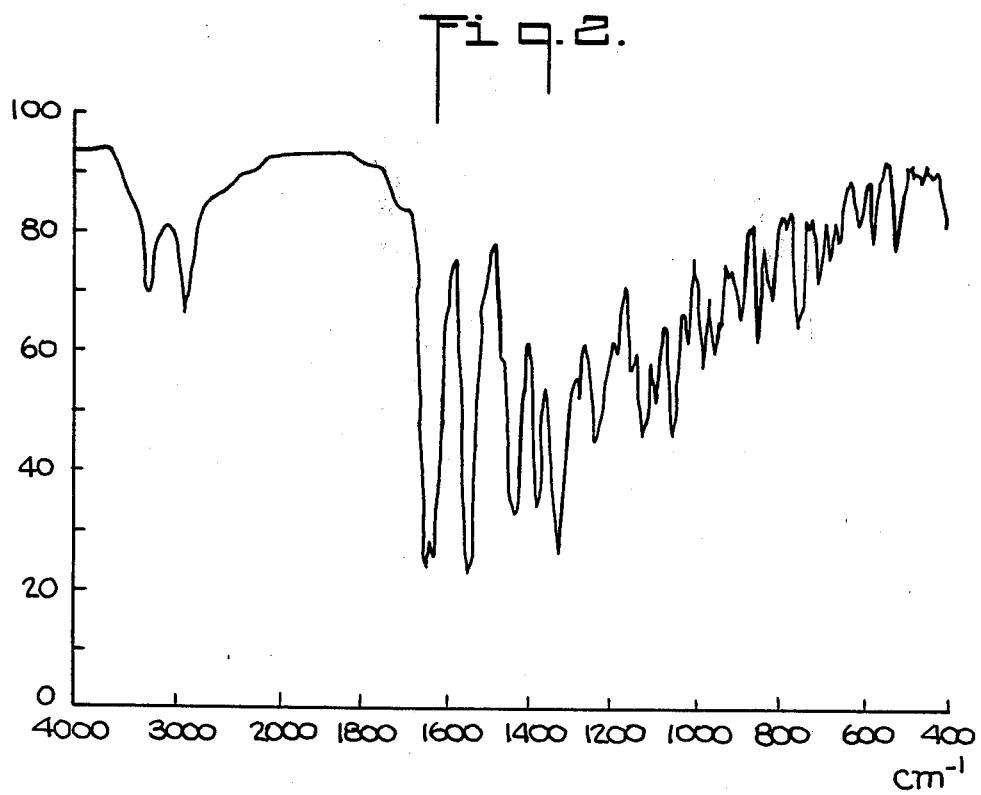

IR spectrum (KBr tablet, cm$^{-1}$), (FIG. 2): 3285(w) (N-H stretch), 1644(vs) (C=C stretch), 1630(vs) (C=O stretch), 1548(C=O stretch)

From the foregoing properties, the substance is identified as 7-deamino-10-decarbamoyloxy-9-dehydro-7-hydroxy-mitomycin C. Yield 66%.

EXAMPLE 10

Preparation of Compound [I-2-2] from Compound [I-7]

In this example, 12 mg of 7-deamino-10-decarbamoyloxy-9-dehydro-7-hydroxy-mitomycin C obtained in Example 9 is dissolved in 3 ml of ethyl acetate. An excess amount of ethyl ether solution of diazomethane is added dropwise to the solution under ice cooling and the mixture is allowed to stand for 10 minutes. The mixture is then concentrated under reduced pressure and the reside is purified by silica gel column chromatography using a mixed solvent of chloroform and acetone (6:4) to obtain 8 mg of purplish black crystals having the following physical properties:

Mass spectrum:

The substance exhibits molecular ion peak at m/e 288. Molecular weight obtained by high resolution mass spectrometry is 288.1120 (288.1110 as calculated).

$^1$HNMR spectrum (in pyridine-d$_5$, δ(ppm)): 1.83(dd,1H), 3.07(d,1H), 3.16(s,3H), 3.53(dd,1H), 4.01(s,3H), 4.33(d,1H), 5.59(d,1H), 6.57(d,1H)

Figure 3:
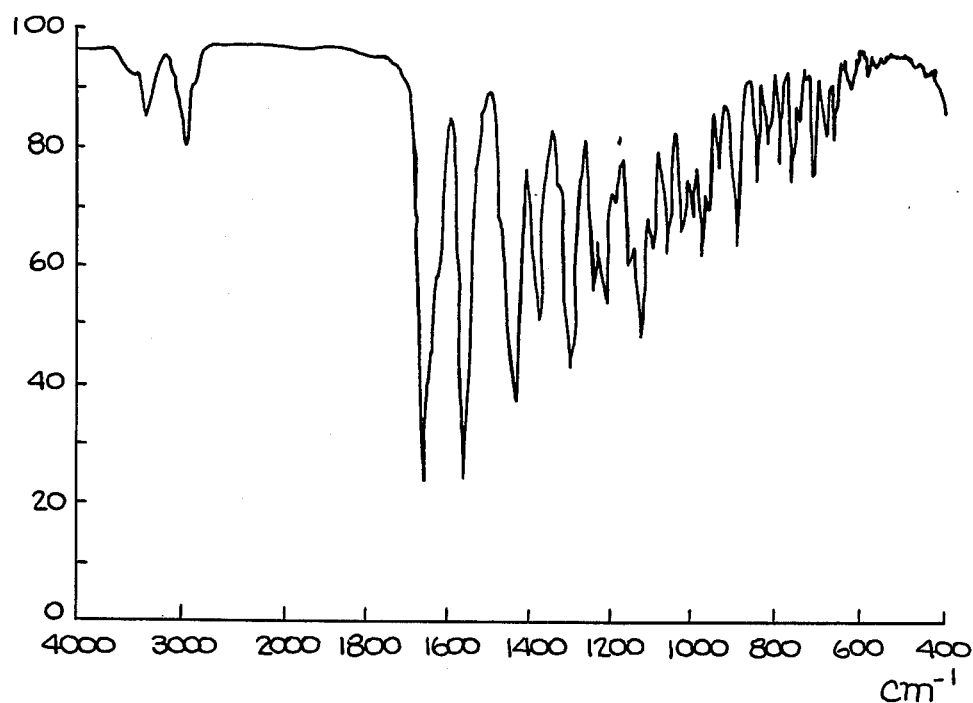

IR spectrum (KBr tablet, cm$^{-1}$), (FIG. 3): 3305(vw) (N-H stretch), 1650(vs) (C=O stretch), 1554(vs) (C=O stretch).

From the foregoing properties, the substance is identified as 10-decarbamoyloxy-9-dehydro-mitomycin A. Yield 63%.

EXAMPLE 11

Preparation of Compound [I-2-1] from Compound [I-2-2]

In this example, 5.2 mg of 10-decarbamoyloxy-9-dehydro-mitomycin A obtained in Example 10 is dissolved in 2 ml of methanol saturated with ammonia. The solution is stirred at room temperature for 2 hours. The solution is then concentrated under reduced pressure and the residue is purified by silica gel column chromatography using a mixed solvent of chloroform and acetone (1:1) to obtain 4.1 mg of deep green crystals.

Mass spectrum, $^1$HNMR spectrum and IR spectrum of the substance are in accord with those of the compound obtained in Example 2. Therefore, the substance is identified as 10-decarbamoyloxy-9-dehydro-mitomycin C. Yield 83%.

EXAMPLE 12

Preparation of Compound [I-8] from Compound [VI]

In this example, 134 mg of 10-decarbamoyloxy-9-dehydro-porfiromycin obtained in Reference Example 4 is dissolved in 25 ml of 0.1N sodium hydroxide. The solution is stirred at room temperature for 4 hours. The reaction solution is adjusted to pH 3 with diluted hydrochloric acid and extracted with ethyl acetate. The extract is washed with water, dried with anhydrous magnesium sulfate and concentrated under reduced pressure. The residue is purified by silica gel column chromatography using a mixed solvent of chloroform and methanol (9:1) and crystallized from a mixed solvent of chloroform and methanol to obtain 115 mg of dark green needle crystals having the following physical properties:

Mass spectrum:

The substance exhibits molecular ion peak at m/e 288.

$^1$HNMR spectrum (in pyridine-d$_5$, δ(ppm)): 2.03(s,3H), 2.12(s,3H), 2.22(dd,1H), 2.48(d,1H), 3.13(s,3H), 3.47(dd,1H), 4.44(d,1H), 5.44(bs,1H), 6.48(bs,1H)

Figure 4:
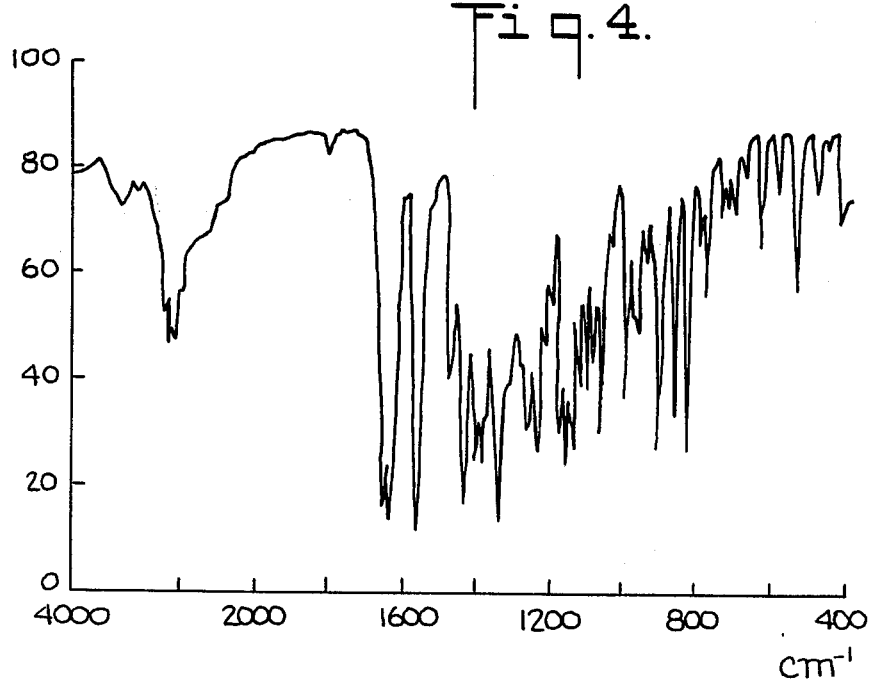

IR spectrum:

IR spectrum (KBr tablet) is shown in FIG. 4.

From the foregoing properties, the substance is identified as 10-decarbamoyloxy-9-dehydro-7-deamino-7-hydroxy-porfiromycin. Yield 85.3%.

REFERENCE EXAMPLE 1

Preparation of Compound [IV] from Compound [V]

In this example, 230 mg of sodium is dissolved in 50 ml of isopropanol and 500 mg of mitomycin C is added to the solution. The mixture is stirred at room temperature for 8 hours. The reaction mixture is then neutralized with an excess amount of dry ice. The precipitate is filtered out and the filtrate is concentrated under reduced pressure. The residue is purified by silica gel column chromatography using a mixed solvent of chloroform and methanol (9:1) to obtain 270 mg of purplish black crystals.

The substance is identified as the known compound 10-decarbamoyl-mitomycin C from melting point, $^1$HNMR spectrum, TLC, and similar properties. Yield 62%.

REFERENCE EXAMPLE 2

Preparation of Compound [III] from Compound [IV]

In this example, 138 mg of 10-decarbamoyl-mitomycin C obtained in Reference Example 1 is dissolved in 1 ml of pyridine. Then, 60 μl of acetic anhydride is added to the solution under ice cooling and sodium chloride and the mixture is stirred in an atmosphere of nitrogen for 1 hour. The reaction mixture is then poured into a saturated aqueous solution of sodium hydrogen carbonate and the mixture is extracted with ethyl acetate. The extract is washed with water, dried with anhydrous sodium sulfate and concentrated under reduced pressure. The residue is then purified by silica gel column chromatography using a mixed solvent of chloroform and methanol (95:5) to obtain 153 mg of purplish black crystals having the following physical properties: Mass spectrum:

The substance exhibits molecular ion peak at m/e 333. $^1$NHMR spectrum (in pyridine-d$_5$, δ(ppm): 2.05(s,3H), 2.23(s,3H), 3.23(s,3H), 3.57(dd,1H), 3.66(dd,1H), 3.94(dd,1H), 3.98(d,1H), 4.33(dd,1H), 4.76(d,1H), 4.84(dd,1H), 7.57(bs,2H)

IR spectrum (KBr tablet, cm$^{-1}$): 3435(m), 3335(m) (N-H stretch), 1694(m), 1605(s), 1555(vs) (C=O stretch)

From the foregoing properties, the substance is identified as 1a-N-acetyl-10-decarbamoyl-mitomycin C. Yield 97%.

REFERENCE EXAMPLE 3

Preparation of Compound [II] from Compound [III]

In this example, 62 mg of 1a-N-acetyl-10-decarbamoylmitomycin C obtained in Reference Example 2 is dissolved in 0.5 ml of anhydrous pyridine. Then, 15 μl of methanesulfonyl chloride is added to the solution in an atmosphere of nitrogen under ice cooling and sodium chloride and the mixture is stirred for 2 hours. The reaction mixture is poured in a saturated aqueous solution of sodium hydrogen carbonate and the mixture is extracted with ethyl acetate. The extract is washed with water, dried with anhydrous sodium sulfate and concentrated under reduced pressure. The residue is purified by silica gel column chromatography using a mixed solvent of chloroform and methanol (96:4) to obtain 74 mg of purplish black crystals having the following physical properties:

$^1$HNMR spectrum (in pyridine-$d_5$, δ(ppm)): 2.04(s,3H), 2.11(s,3H), 3.20(s,3H), 3.46(s,3H), 3.60(dd,1H), 3.61(dd,1H), 3.79(d,1H), 4.09(dd,1H), 4.84(dd,1H), 5.58(dd,1H), 7.71(bs,2H)

IR spectrum (KBr tablet, cm$^{-1}$): 3445(w), 3235(m) (N-H stretch), 1697(s), 1605(s), 1563(vs) (C=O stretch), 1350(vs) (antisym. SO$_2$ stretch), 1173(vs) (sym. SO$_2$ stretch)

From the foregoing properties, the substance is identified as 1a-N-acetyl-10-decarbamoyl-10-methanesulfonylmitomycin C. Yield 97%.

REFERENCE EXAMPLE 4

Synthesis of Compound [VI]

In this example, 500 mg of porfiromycin is added to 150 ml of isopropanol containing 1.5 g of sodium isopropoxide. The mixture is stirred at room temperature for 6 hours. The reaction mixture is neutralized with an excess amount of dry ice and the deposit is filtered out. The filtrate is then concentrated under reduced pressure and the residue is purified by silica gel column chromatography using a mixed solvent of chloroform and methanol (94:6) to obtain 299 mg of purplish blue crystals having the following physical properties:

$^1$HNMR spectrum (in CD$_3$OD, δ(ppm)): 1.75(s,3H), 2.29(s,3H), 2.45(dd,1H), 2.54(d,1H), 3.20(s,3H), 3.34(dd,1H), 3.46(dd,1H), 3.80(dd,1H), 4.09(dd,1H), 4.16(d,1H)

From the foregoing properties, the substance is identified as 10-decarbamoyl-porfiromycin. Yield 68.2%.

Thereupon, 105.4 mg of 10-decarbamoyl-porfiromycin is dissolved in 2 ml of anhydrous pyridine. Then, 0.05 ml of methanesulfonyl chloride is added to the solution and the mixture is stirred for 20 minutes. The reaction mixture is poured into 10 ml of a saturated aqeuous solution of sodium hydrogen carbonate and the mixture is extracted with ethyl acetate. The extract is washed with water, dried with anhydrous sodium sulfate and concentrated under reduced pressure. The residue is purified by silica gel column chromatography using a mixed solvent of chloroform and methanol (95:5) to obtain 130.7 mg of purple solid having the following physical properties: Mass spectrum:

The substance exhibits molecular ion peak at m/e 383.

$^1$HNMR spectrum (in CD$_3$OD, δ(ppm)): 1.74(s,3H), 2.33(s,3H), 2.45(dd,1H), 2.53(d,1H), 3.18(s,3H), 3.22(s,3H), 3.46(dd,1H), 3.62(dd,1H), 4.19(d,1H), 4.42(dd,1H), 4.82(dd,1H)

From the foregoing properties, the substance is identified as 10-decarbamoyl-10-methanesulfonyl-porfiromycin. Yield 98.6%.

Thereafter, 17 mg of 10-decarbamoyl-10-methanesulfonyl-porfiromycin, as thus obtained is dissolved in 1 ml of anhydrous tetrahydrofuran. Then, 54 mg of 1,5-diazabicyclo[5.4.0]undecene-5 is added to the solution and the mixture is refluxed in an atmosphere of nitrogen for 5 hours. The reaction mixture is then concentrated under reduced pressure and the residue is purified by silica gel column chromatography using a mixed solvent of chloroform and acetone (4:1) to obtain 7.5 mg of purplish blue crystals having the following physical properties:

Mass spectrum:

The substance exhibits molecular ion peak at m/e 287.

$^1$HNMR spectrum (in CD$_3$OD, δ(ppm)): 1.78(s,3H), 2.21(s,3H), 2.44(bs,2H), 3.06(s,3H), 3.42(dd,1H, 4.26(d,1H), 5.34(d,1H), 6.08(d,1H)

From the above properties, the substance is identified as 10-decarbamoyloxy-9-dehydro-porfiromycin. Yield 58.9%.

What is claimed is:

1. A compound of the formula

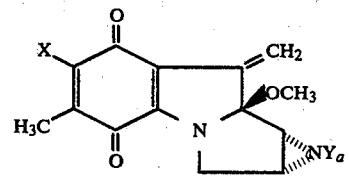

wherein Ya is a hydrogen atom or a methyl group and when Ya is a hydrogen atom, X is an amino group, an hydroxy group or an alkoxy group having 1–4 carbon atoms and when Ya is a methyl group, X is an hydroxy group.

2. A compound according to claim 1 wherein Ya is a hydrogen atom and X is an amino group.

3. A compound according to claim 1 wherein Ya is a hydrogen atom and X is a hydroxy group.

4. A compound according to claim 1 wherein Ya is a hydrogen atom and X is a methoxy group.

5. A compound according to claim 1 wherein Ya is a methyl group and X is a hydroxy group.

* * * * *